Figure 1:
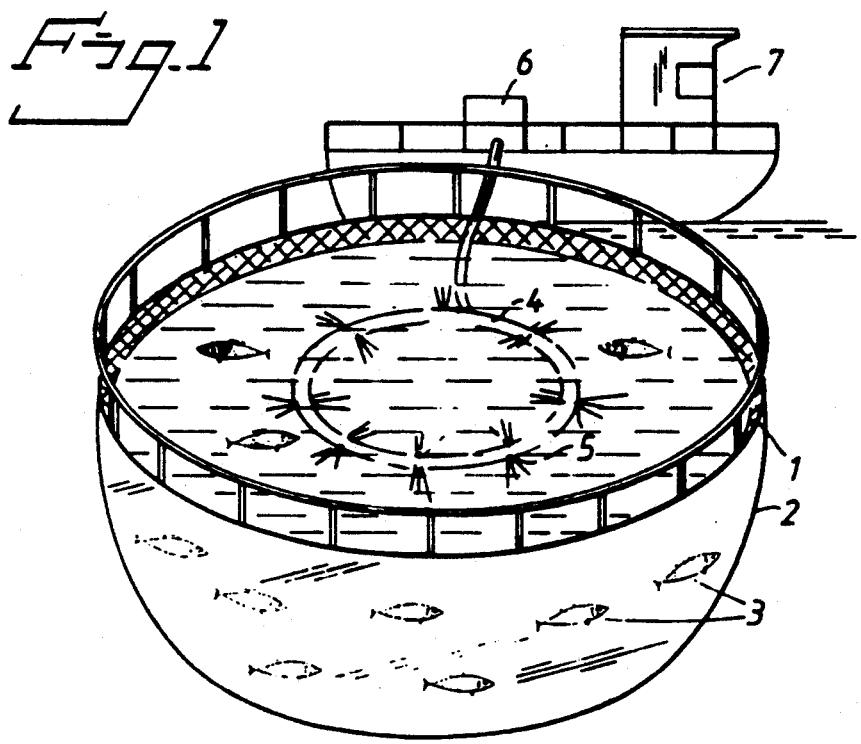

United States Patent [19]
Thomassen et al.

[11] Patent Number: 5,313,911
[45] Date of Patent: May 24, 1994

[54] METHOD FOR CONTROLLING AQUATIC PARASITES

[75] Inventors: Jan M. Thomassen, Bådalen; Odd I. Lekang, Oslo, both of Norway

[73] Assignee: Eka Nobel AB, Bohus, Sweden

[21] Appl. No.: 963,693

[22] Filed: Oct. 20, 1992

[30] Foreign Application Priority Data

Oct. 24, 1991 [SE] Sweden .................. 9103113-8

[51] Int. Cl.$^5$ .................................. A01K 61/00
[52] U.S. Cl. ........................ 119/231; 119/268
[58] Field of Search ............ 119/3, 231, 268, 214, 119/243; 426/2; 424/616

[56] References Cited

U.S. PATENT DOCUMENTS

| | | | |
|---|---|---|---|
| 4,289,728 | 9/1981 | Peel et al. | 422/24 |
| 4,926,795 | 5/1990 | Hamilton et al. | 119/3 |

FOREIGN PATENT DOCUMENTS

| | | | |
|---|---|---|---|
| 0035800 | 9/1981 | European Pat. Off. | |
| 0347731 | 12/1989 | European Pat. Off. | |
| 0141142 | 11/1980 | Japan | 119/3 |
| 1-317346 | 12/1989 | Japan | |
| 3108428 | 5/1991 | Japan | 119/3 |
| 1210254 | 11/1986 | U.S.S.R. | 119/3 |

OTHER PUBLICATIONS

WPI Abstract 91-300222/41, abstract of JP 030200705, "New hydrogen peroxide formulation used in water--comprises porous support of inorganic material impregnated with aq. hydrogen peroxide soln".

WPI Abstract 90-040628/06, abstract of JP 010317346, "Repelling ectoparasite(s) for salt water fish culture--comprises washing fish by adding hydrogen peroxide to closed area and then opening shutter".

WPI Abstract 71-677015/42, abstract of JP 710035867, "Agent for exterminating external parasites of fish".

WPI Abstract 67-00755H/00, abstract of JP 670023242, "Piscine ectoparasiticides con a cpd. or compn. of phosphoric acid salts of poly-(or condensed)-phosphoric acid salts with hydrogen peroxide, as a main component".

Primary Examiner—Gene Mancene
Assistant Examiner—Todd E. Manahan
Attorney, Agent, or Firm—Burns, Doane, Swecker & Mathis

[57] ABSTRACT

An agent for controlling parasites on fish consists of an aqueous solution containing more than 1.2 but less than 2.9 g $H_2O_2$ per liter. Disclosed are also a method for preparing such an agent and a method for controlling parasites in fish breeding.

9 Claims, 1 Drawing Sheet

METHOD FOR CONTROLLING AQUATIC PARASITES

The present invention relates to an agent for controlling parasites on fish, said agent consisting of an aqueous solution containing more than 1.2, but less than 2.9 g $H_2O_2$ per liter. The invention also relates to a method for preparing an agent for controlling parasites, and to a method for controlling parasites in fish breeding.

In connection with fish breeding, parasites cause major problems if not efficiently controlled. Salmon breeding generally meets with problems occasioned by salmon louse (*Lepeophtheirus salmonis*), a small crustacean which can attach to the fish. If the salmon lice are not controlled the output and hence the economic yield of the fish breeding will drop. Usually, salmon lice are controlled with different organophosphates, such as dichlorovos or trichlorophon, which are acetylcholinesterase-inhibiting substances. Thus, they are toxic both to fish and to man, and also are not considered environmentally-friendly. Nor are these agents effective against salmon lice in the fry state, but only against adult and half-grown salmon lice. Salmon lice resistant to the agents employed have also been encountered.

JP Published Patent Application 89-317346 discloses the use of hydrogen peroxide for killing parasites on certain fish species. For optimum results, contents of from 400 to 1000 ppm hydrogen peroxide are recommended for use during a time of from 1 to 20 min. It has however been found that this treatment is not effective on salmon lice.

The object of the invention is to provide an environmentally-friendly method which is efficacious in connection with fish breeding for destroying salmon lice and which should not endanger the life of salmon in a fish breeding facility or cause any major harm to the salmon.

The invention relates to an agent for controlling parasites, preferably salmon lice (*Lepeophtheirus salmonis*), in the breeding of fish, preferably from the salmon family. The agent of the invention consists of an aqueous solution containing more than 1.2, preferably more than about 1.3, particularly more than about 1.4 g $H_2O_2$ per liter. Suitably, the $H_2O_2$-content is below about 2.9, preferably below about 2.7 g per liter. Further, the aqueous solution may contain from about 20 to about 40, preferably from about 27 to about 35 per thousand salts based on the weight, which salts may have substantially the same composition as in sea-water, i.e. consist of from about 70 to about 90% by weight of NaCl, the balance substantially being $MgCl_2$, $MgSO_4$, $CaSO_4$, $K_2SO_4$, $CaCO_3$ and $MgBr_2$. The aqueous solution suitably has a temperature of from 0° to about 20° C. In order to avoid killing of the fish, the temperature is preferably from 0° to 14° C.

The invention also relates to a method for preparing an agent for controlling parasites, preferably salmon lice, in the breeding of fish, preferably from the salmon family. The agent is prepared in that the water in a fish-breeding facility, generally sea-water containing from about 20 to about 40, preferably from about 27 to about 35 per thousand salts based on the weight and suitably having a temperature of from 0° to about 20° C., preferably from 0° to 14° C., is supplied with hydrogen peroxide or a hydrogen-peroxide-producing substance, such that the $H_2O_2$-content in the water is above 1.2, preferably above about 1.3, especially above about 1.4 g per liter, but below about 5, preferably below about 2.9, especially below about 2.7 g per liter. Preferably, the additions are made so that the $H_2O_2$-content is maintained within the above-mentioned ranges at least for a time exceeding 20 min. Preferably, the hydrogen peroxide content is maintained within the above-mentioned ranges for a time up to between 20 and 60 min, preferably for a time up to between 20 and 30 min. Suitably, a certain volume of water containing fish and parasites is screened off, so that the exchange with the surrounding water is essentially stopped, whereupon the screened-off water is supplied with a suitable amount of hydrogen peroxide. The water volume may be, for instance, from about 10 to about 2000 $m^3$, preferably from about 200 to about 1600 $m^3$, and contain, for instance, from about 1 to about 100 tonnes of fish. The water can be screened off by enclosing a fish-holding string bag with a substantially water-impermeable cover, for instance a plastic tarpaulin, so as to form a bag which encloses the fish and the parasites, and which preferably is open only above the water surface. It is also preferred that the volume of the string bag be reduced by lifting its bottom and/or moving its walls together. Preferably, the hydrogen peroxide is supplied during as short a time as possible, without the concentration gradients becoming too high, e.g. during a time of from about 2 to about 10 min, depending on the water volume, in such an amount that a suitable $H_2O_2$-content is maintained for a suitable time, i.e. at least 20 min. After this time, the water-impermeable cover is removed so that the water exchange with the surroundings is resumed and the hydrogen peroxide is rapidly diluted. Since it has proved essential that the concentration gradients of the hydrogen peroxide in the water be minimised, the hydrogen peroxide should be supplied to the water by a substantially uniform distribution. According to a preferred method, the hydrogen peroxide is added in the form of an aqueous solution through a pipe or a hose having a plurality of nozzles disposed below the water surface, the tube or hose preferably being in the form of a closed, substantially horizontal annulus disposed below the water surface. Such an annulus can be provided by connecting a hose or a pipe to a T-branch connection, in turn connected to a source of hydrogen peroxide, for instance a supply tank. The annulus may for instance have a diameter of from about 1 to about 6 m, preferably from about 2 to about 5 m, and have from about 10 to about 100, preferably from about 30 to about 70 holes serving as nozzles. It is also preferred that the hydrogen peroxide be supplied in the form of an aqueous solution containing from about 10 to about 70% by weight of $H_2O_2$, especially from about 25 to about 55% by weight of $H_2O_2$. To ensure a suitable $H_2O_2$-content in the water for a sufficient period of time, it is preferred that this content is measured by a method conformed to field analysis. A preferred such method of analysis comprises the steps of supplying a number of vessels, e.g. test tubes or flasks, with the same amount of water, each vessel containing different predetermined amounts of reagent for $H_2O_2$, e.g. $KMnO_4$, thus making it possible to estimate the $H_2O_2$-content of the water.

Finally, the invention relates to a method for controlling parasites in fish breeding, for instance salmon lice, by subjecting them to an agent prepared according to the invention, suitably for a time exceeding 20 min, preferably from 20 to about 60 min, especially from 20 to about 30 min. It has been found that a treatment time above 20 min is required for killing salmon lice to an adequate extent, even if the $H_2O_2$-content is high. It has also been found that treatment times exceeding about 60 min are harmful to the fishes in the breeding facility, even if the $H_2O_2$-content is low. Further, it has been found that treatment at too high water temperature is harmful to the fish, for which reason the preferred temperature is within the range from 0° to 14° C. Preferably, the parasites are destroyed in that the fishes and the parasites are enclosed, together with the water in which they live, in a bag and are subjected to hydrogen peroxide, as described in connection with the method of preparing the agent according to the invention. The treatment is ended by removing the bag, so that the water with hydrogen peroxide is diluted with the surrounding water.

Figure 2:
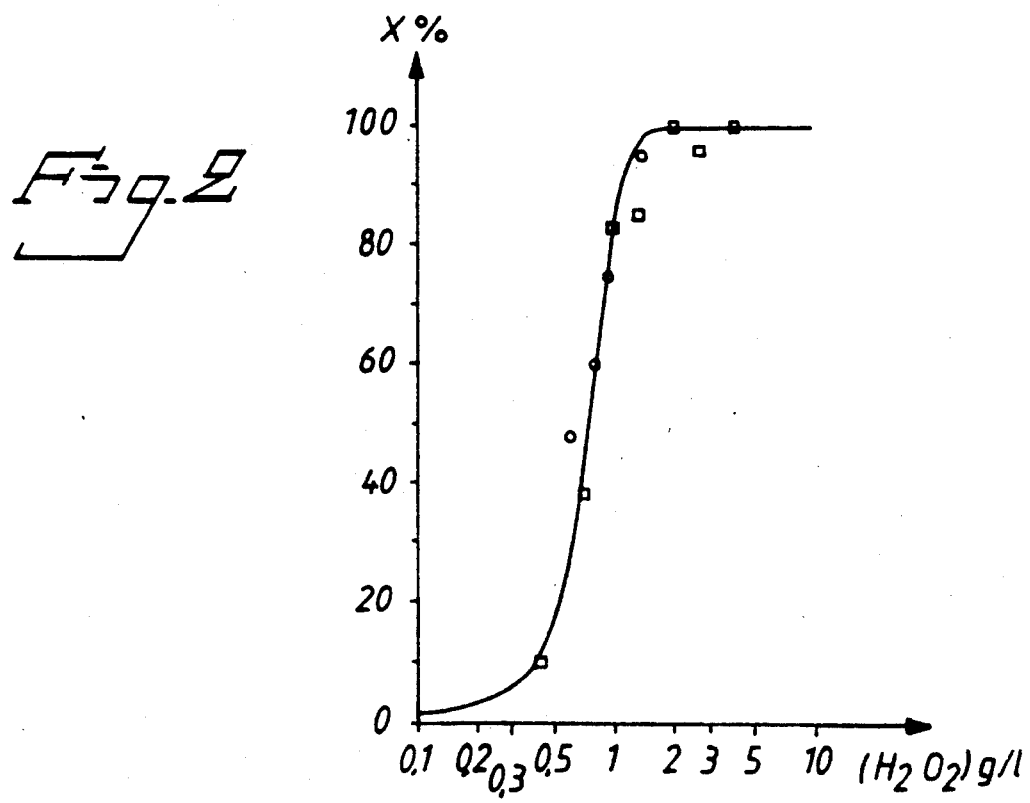

FIG. 1 shows an example of how the water in a fish breeding plant can be supplied with hydrogen peroxide, and FIG. 2 shows the dependency of the degree of delousing on the hydrogen peroxide content of the water.

FIG. 1 shows how the fishes 3 in the breeding plant are enclosed by a string bag 1, around which there is disposed an external, substantially water-impermeable plastic tarpaulin 2 forming a bag which is open only above the water surface. Hydrogen peroxide solution is supplied from a tank 6 on a boat 7 through an annular plastic hose 4 disposed below the water surface and having holes 5 serving as nozzles.

The invention will now be illustrated by the following Example which, however, is not intended to restrict the invention. Unless otherwise indicated, all contents are given in parts by weight.

EXAMPLE

Destruction of salmon lice with hydrogen peroxide of different concentrations was carried out in a fish breeding facility in the North Sea according to the following description. The water temperature was between 6° and 14° C.

Tests 1-3 were performed in small string bags (3×3×3 m) containing 100 salmon weighing 1-2 kg. The bottom of the string bags was pulled up to a depth of 1-1.5 m, and a plastic tarpaulin was passed underneath and around the string bag so as to form a salmon-holding bag, to which a 35% hydrogen peroxide solution was supplied. After 20 min, the tarpaulin was removed, except in Tests 3.1 and 3.2, where this was done after 120 and 60 min, respectively. In Tests 1.1 and 1.2, the hydrogen peroxide content of the water was calculated on the basis of the amount supplied, while the content in the other tests was determined by iodometric titration. Before and after each treatment, the number of lice was counted on 5-10 fishes and the degree of delousing was calculated.

Tests 4, 5, 6 and 7 were performed in string bags having a circumference of 40 m, the bottom of the string bags was pulled up to a depth of about 2-3 m, and the bags were provided with an external plastic tarpaulin. In Tests 4, 6 and 7, each string bag contained about 2000 salmon weighing 0.5-1 kg, while the string bag in Test 5 contained about 1500-2000 rainbow trout weighing 1.5-2.5 kg. In Tests 4 and 5, 35% hydrogen peroxide was pumped out into the bag after dilution with equal parts of sea-water. In Tests 6 and 7, 35% hydrogen peroxide was pumped out into the bag through an annular hose system, as shown in FIG. 1. In all the cases, the hydrogen peroxide was supplied in less than about 5 min, and the tarpaulin was removed 20 min after the hydrogen peroxide supply had been ended. The hydrogen peroxide content of the water was determined by iodometric titration. The amount of lice was counted on 6-12 fishes before and after the treatment.

The results of all the tests appear from the Table below. The number of salmon lice before and after each treatment is given as the mean value for the examined fishes. The degree of delousing X in per cent in relation to the hydrogen peroxide content of the water is also graphically represented in FIG. 2.

| Test No. | Amount 35% $H_2O_2$ (l) | Content $H_2O_2$ g/l | Number of salmon lice before | Number of salmon lice after | Delousing degree (%) |
|---|---|---|---|---|---|
| 1.1 | 90 | 3.5-5 | 21 | 0 | 100 |
| 1.2 | 30 | 1.5-2 | 29 | 0 | 100 |
| 2.1 | 30 | 2.7 | 78 | 5 | 94 |
| 2.2 | 15 | 1.0 | 52 | 9 | 83 |
| 3.1 | 7.5 | 0.42 | 87 | 78 | 10 |
| 3.2 | 10 | 0.7 | 84 | 32 | 38 |
| 3.3 | 20 | 1.34 | 92 | 14 | 85 |
| 4 | 400 | 0.6 | 19.6 | 10.2 | 48 |
| 5 | 760 | 1.4 | 51 | 2.6 | 95 |
| 6 | 760 | 0.8 | 122 | 49 | 60 |
| 7 | 760 | 0.95 | 131 | 33 | 75 |

The results show that the effect of the treatment is considerably enhanced when the hydrogen peroxide content is raised from 1 to 1.5 g per liter, which must be considered most surprising.

We claim:

1. A method for controlling parasites in fish breeding, comprising supplying the water in which fish are maintained in a fish breeding facility with hydrogen peroxide or a hydrogen peroxide-producing substance, in an amount sufficient to provide an $H_2O_2$ content in the water above about 1.2 but below about 2.9 g per liter.

2. A method as claimed in claim 1, wherein the $H_2O_2$ content in the water is maintained within the stated range for more than about 20 min.

3. A method as claimed in claim 1, wherein the temperature of said water in which the fish are maintained is from about 0° to about 14° C.

4. A method for controlling parasites in fish breeding, comprising supplying the water in a fish breeding facility with hydrogen peroxide or a hydrogen peroxide-producing substance, in an amount sufficient to provide an $H_2O_2$ content in the water above about 1.2 but below about 5 g per liter and maintaining the $H_2O_2$ content within this range for more than about 20 min.

5. A method as claimed in claim 4, wherein the $H_2O_2$ content in the aqueous solution exceeds about 1.3 $H_2O_2$.

6. A method for controlling salmon lice (*Lepeophtheirus salmonis*) in fish breeding, comprising supplying the water in a fish breeding facility with hydrogen peroxide or a hydrogen peroxide-producing substance in an amount sufficient to produce an $H_2O_2$ content in the water above about 1.2 but below about 5 g per liter.

7. A method as claimed in claim 6, wherein the $H_2O_2$ content in the water is maintained within the stated range for more than about 20 min.

8. A method for controlling parasites in fish breeding, comprising subjecting the parasites to an aqueous solution containing more than about 1.2 g but less than about 2.9 g $H_2O_2$ per liter.

9. A method for controlling salmon lice (*Lepeophtheirus salmonis*) in fish breeding, comprising subjecting said lice to an aqueous solution containing more than about 1.2 g but less than about 5 g $H_2O_2$ per liter.

* * * * *